US012310690B2

(12) United States Patent
Blake et al.

(10) Patent No.: US 12,310,690 B2
(45) Date of Patent: May 27, 2025

(54) CHARACTERISING THE PERFORMANCE OF A ROBOTIC JOINT

(71) Applicant: CMR SURGICAL LIMITED, Cambridge (GB)

(72) Inventors: Martin Joseph Blake, Cambridge (GB); Andrew John Hazell, Cambridge (GB); Matthew John Reynolds, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 336 days.

(21) Appl. No.: 18/013,594

(22) PCT Filed: Jul. 2, 2021

(86) PCT No.: PCT/GB2021/051682
§ 371 (c)(1),
(2) Date: Dec. 29, 2022

(87) PCT Pub. No.: WO2022/008880
PCT Pub. Date: Jan. 13, 2022

(65) Prior Publication Data
US 2023/0240778 A1    Aug. 3, 2023

(30) Foreign Application Priority Data
Jul. 6, 2020 (GB) ...................... 2010357

(51) Int. Cl.
*A61B 34/00* (2016.01)
*A61B 34/37* (2016.01)
(Continued)

(52) U.S. Cl.
CPC .............. *A61B 34/37* (2016.02); *A61B 34/74* (2016.02); *A61B 90/06* (2016.02); *B25J 9/1025* (2013.01);
(Continued)

(58) Field of Classification Search
CPC ......... A61B 34/37; A61B 34/74; A61B 90/06; A61B 2034/305; A61B 2090/066;
(Continued)

(56) References Cited

U.S. PATENT DOCUMENTS

| 5,418,441 | A  | 5/1995 | Furukawa |
| 2011/0204838 | A1 | 8/2011 | Nakasugi |

(Continued)

FOREIGN PATENT DOCUMENTS

| JP | H04233602 A | 8/1992 |
| JP | 2014161952 A | 9/2014 |

(Continued)

OTHER PUBLICATIONS

Claire Dumas et al: "Joint stiffness identification of six-revolute industrial serial robots", Robotics and Computer Integrated Manufacturing, vol. 27, No. 4, Feb. 26, 2011 (Feb. 26, 2011), pp. 881-888, XP055569853, GB, ISSN: 0736-5845.

(Continued)

*Primary Examiner* — Ian Jen
(74) *Attorney, Agent, or Firm* — Lando & Anastasi, LLP

(57) ABSTRACT

A method for characterising the performance of a joint in a surgical robotic arm, the joint being driven by a drivetrain which transfers power from a drive source to the joint, the method comprising: sending a first command signal to position the robot arm into an initial configuration; sending a second command signal to apply a force to the joint to displace the joint from a steady state; for a plurality of predefined time intervals: receiving a first measurement indicating the configuration of the drive source at a first end of the drivetrain; receiving a second measurement indicating the configuration of the joint at a second end of the drivetrain; calculating a value of elongation using the first and second measurements; and receiving a third measurement (Continued)

indicating the torque experienced by the joint at the second end of the drivetrain; comparing the values of elongation with corresponding values of torque at each of the pre-defined time intervals; and generating an output from the comparison indicating the performance of the joint.

19 Claims, 3 Drawing Sheets

(51) Int. Cl.
    *A61B 90/00*     (2016.01)
    *B25J 9/10*     (2006.01)
    *B25J 9/16*     (2006.01)
    *A61B 34/30*     (2016.01)

(52) U.S. Cl.
    CPC .......... *B25J 9/1641* (2013.01); *B25J 9/1653* (2013.01); *A61B 2034/305* (2016.02); *A61B 2090/066* (2016.02)

(58) Field of Classification Search
    CPC ...... B25J 9/1025; B25J 9/1641; B25J 9/1653; G05B 2219/39186; G05B 2219/45117
    See application file for complete search history.

(56) References Cited

U.S. PATENT DOCUMENTS

| | | |
|---|---|---|
| 2015/0248121 A1 | 9/2015 | Nilsson |
| 2015/0250547 A1 | 9/2015 | Fukushima et al. |
| 2017/0015004 A1 | 1/2017 | Osaka et al. |
| 2022/0105628 A1* | 4/2022 | Madsen ................ B25J 13/088 |

FOREIGN PATENT DOCUMENTS

| | | |
|---|---|---|
| WO | 2015046081 A1 | 4/2015 |
| WO | 2020053195 A1 | 3/2020 |

OTHER PUBLICATIONS

Notification of Transmittal of the International Search Report and the Written Opinion of the International Searching Authority from corresponding PCT/GB2021/051682 dated Oct. 11, 2021.
United Kingdom Search Report from corresponding United Kingdom Application No. 2010357.8 dated Dec. 18, 2020.
United Kingdom Corrected Search Report from corresponding United Kingdom Application No. 2010357.8 dated Dec. 18, 2020.
Indian Examination Report from corresponding Indian Application No. 202327007310 dated Apr. 6, 2023.
Japanese Notification of Reason for Rejection from corresponding Japanese Patent Application No. 2022-508959 mailed Mar. 14, 2023.

* cited by examiner

CHARACTERISING THE PERFORMANCE OF A ROBOTIC JOINT

CROSS-REFERENCE TO RELATED APPLICATIONS

This application is a U.S. National Phase Application under 35 U.S.C. § 371 of International Application No. PCT/GB2021/051682, filed Jul. 2, 2021, which claims priority to United Kingdom Application No. 2010357.8, filed Jul. 6, 2020. Each application referenced above is hereby incorporated by reference in its entirety for all purposes.

FIELD OF THE INVENTION

This invention relates to a test for characterising the performance of a joint in a surgical robotic arm.

BACKGROUND OF THE INVENTION

A typical robotic manipulator comprises a series of rigid elements that are coupled together by one or more joints, which may be joined in series to form an arm. The manipulator further comprises a base unit at a first end of the series of rigid elements, and an end effector at a second end that opposes the first end. Each joint of the manipulator is driven by a drive source and a corresponding drivetrain so as to cause relative motion of the rigid elements. This relative motion is used to vary the configuration of the end effector at a desired location. Each joint may provide rotational motion and/or linear motion. The drive source may be any suitable means, such as an electronic motor or a hydraulic actuator.

The drivetrain associated with a given joint typically comprises a gearbox. The gearbox enables the variation of force from the drive source that is applied to the joint. A typical gearbox includes gears or teethed components to slippage within the drivetrain. The use of teethed components results in clearances, and ultimately a loss of motion, within the drivetrain at certain joint configurations. This loss of motion, and its effect on joint configuration, is difficult to anticipate. There is therefore a need to test and obtain real-world data indicating the performance of a joint at a range of different configurations. Knowledge of the performance of a joint and its corresponding drive mechanism is advantageous for obtaining parameters against which to compare and determine the performance of the joint during its use and enables the tuning of control parameters provided to the drive source. There are a number of known tests for characterising the performance of a robotic joint. These known tests typically comprise the use of external test equipment and sensors. Testing, may, for example, involve locking one of the ends of the drivetrain while forcing the other end of the drivetrain to rotate in order to measure the torque and configuration of the joint at the unlocked end of the drivetrain. Alternatively, or in addition, to this a known test comprises manually applying a force to a joint in the robot arm and monitoring the variation in input and output joint configuration as this torque is applied. A disadvantage associated with the use of external equipment and sensors to characterise joint performance is that it introduces complexity and reliability issues into the test procedure. In addition to this, known test methods do not enable a whole range of joint configurations and forces to be observed. Thus, a full spectrum of data points required for a thorough investigation of joint performance cannot be obtained.

There is a need for an automated, quick, reliable and standardised test for characterising the performance of a robotic joint.

SUMMARY OF THE INVENTION

According to a first aspect, there is provided a method for characterising the performance of a joint in a surgical robotic arm, the joint being driven by a drivetrain which transfers power from a drive source to the joint, the method comprising: sending a first command signal to position the robot arm into an initial configuration; sending a second command signal to apply a force to the joint to displace the joint from a steady state; for a plurality of predefined time intervals: receiving a first measurement indicating the configuration of the drive source at a first end of the drivetrain; receiving a second measurement indicating the configuration of the joint at a second end of the drivetrain; calculating a value of elongation using the first and second measurements; and receiving a third measurement indicating the torque experienced by the joint at the second end of the drivetrain; comparing the values of elongation with corresponding values of torque at each of the predefined time intervals; and generating an output from the comparison indicating the performance of the joint.

Generating the output may comprise calculating a graph of elongation against torque to define a stiffness characteristic for the joint.

The method may further comprise comparing the values of elongation and corresponding values of torque to a predetermined characteristic for the joint.

The method may further comprise sending a command signal to apply an instantaneous force to the displace the joint from the steady state; and receiving the first, second and third measurements at a plurality of predefined time intervals whilst the joint returns to the steady state.

The method may further comprise sending a command signal to consistently increase the frequency of the force applied to the joint; and receiving the first, second and third measurements at a plurality of predefined time intervals.

The method may further comprise sending a command signal to consistently vary the direction of the force to be applied to the joint; and receiving the first, second and third measurements at a plurality of predefined time intervals.

The second command signal may indicate a desired configuration for the joint.

Elongation may be characterised as the difference between the measured configuration of the drive source $q_i$ and the measured configuration of the joint $q_o$.

The method may further comprise calculating one or more regression lines on the graph of elongation against torque, each regression line having a corresponding gradient.

The method may further comprise analysing the gradients of the one or more regression lines to identify a plurality of distinct regions.

The method may further comprise identifying a backlash region from the graph, the backlash region being characterised a regression line with a near-zero gradient.

The method may further comprise identifying one or more linear stiffness regions from the graph, each linear stiffness region being identified by a regression line with a gradient that is above a predetermined threshold.

The method may further comprise analysing the graph to establish the accuracy of the one or more regression lines.

Analysing the graph may comprise performing an R-squared analysis.

The plurality of distinct regions may be identified by applying signal conditioning to the received sensor measurements.

The drive source may be a motor.

The predetermined configuration of the arm may be selected from a set of predetermined arm configurations.

The drivetrain may comprise one or more gears.

The drivetrain may be a harmonic drive.

DETAILED DESCRIPTION

The present invention will now be described by way of example with reference to the accompanying drawings. In the drawings.

Figure 1:
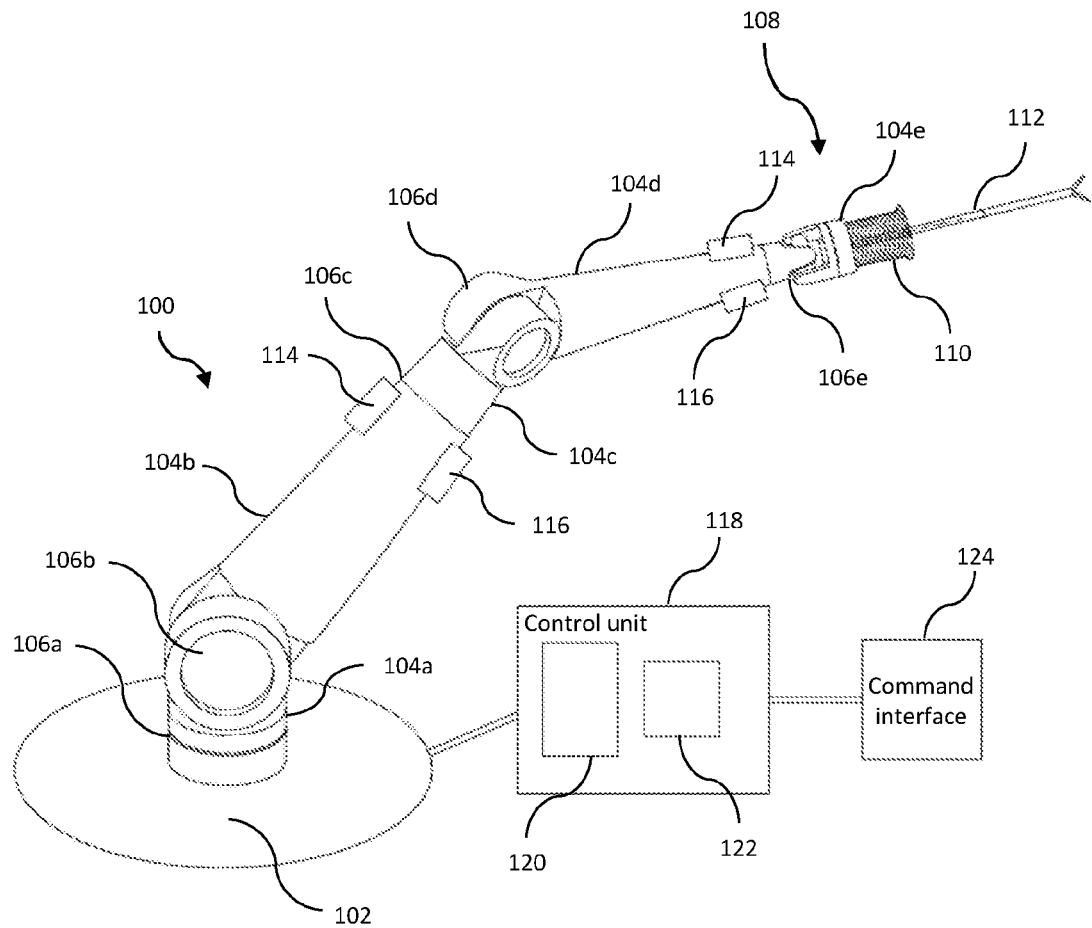
FIG. 1 illustrates the configuration of a robot arm.

The following description describes the present techniques within the context of robotic systems. Robotic systems can include manufacturing systems, such as vehicle manufacturing systems, parts handling systems, laboratory systems, and manipulators such as for hazardous materials or surgical manipulators. The robotic system illustrated in FIG. 1 is specifically a surgical robotic system. However, the features described below are not limited to such a system but are applicable to robotic systems more generally.

FIG. 1 illustrates a surgical robot having an arm 100 which extends from a base unit 102. The arm comprises a plurality of rigid limbs 104a-e which are coupled by a plurality of revolute joints 106a-e. The revolute joints 106a-e are configured to apply rotational motion. Instead of or in addition to these revolute joints, the surgical robot may comprise a one or more joints for providing linear motion. The limb that is closest to the base unit 102 is the most proximal limb 104a and is coupled to the base unit by a proximal joint 106a. The remaining limbs of the arm are each coupled in series by a joint of the plurality of joints 106b-e. A wrist 108 may comprise four individual revolute joints. The wrist 108 couples one limb (104d) to the most distal limb (104e) of the arm. The most distal limb 104e carries an attachment 110 for a surgical instrument 112. Each joint 106a-e of the arm 100 has one or more drive sources 114 which can be operated to cause rotational motion at the respective joint. Each drive source 114 is connected to its respective joint 106a-e by a drivetrain which transfers power from the drive source to the joint. In one example the drivetrain comprises one or more gears. In a more specific example, the drivetrain is a harmonic drive. A harmonic drive comprises the concentric arrangement of a wave generator, a flex spline and a circular spline, and increases the torque that can be applied to the joint by the drive source.

In one example, the drive sources 114 are motors. The drive sources 114 may alternatively be hydraulic actuators, or any other suitable means. Each joint 106a-e further comprises one or more configuration and/or force sensor 116 which provides information regarding the current configuration and/or force at that joint. Where the joint is a revolute joint, one or more of the sensors 116 may be a torque sensor. Where the joint is configured to provide linear motion, one of the one or more sensors 116 may be a strain gauge. In addition to configuration and/or force data, the one or more sensors 116 may additionally provide information regarding the temperature, current or pressure (such as hydraulic pressure). In one example, the one or more configuration sensors are position sensors. That is, the configuration sensors may measure the physical position of the joint. In such an example, one or more of the sensors 116 may be an encoder. An encoder is a position sensor which transforms a position measurement into an electronic signal. The encoder 116 may be a linear or a rotary encoder.

The drive sources 114 are arranged proximally of the joints whose motion they drive, so as to improve weight distribution. For clarity, only some of the drive sources and sensors are illustrated in FIG. 1. It can also be appreciated that the surgical robot 100 may comprise more or fewer limbs and joints than those illustrated in FIG. 1.

The instrument 112 of the surgical robot 100 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser or a suctioner. The instrument further comprises an instrument shaft and an articulation located between the instrument shaft and the end effector. The articulation comprises several joints which permit the end effector to move relative to the shaft of the instrument.

Configuration controllers for the drive sources 114 and sensors 116 are distributed within the robot arm 100. The controllers are connected via a communication bus to a control unit 118. The control unit 118 comprises a processor 120 and a memory 122. The memory 122 stores, in a non-transient way, software that is executable by the processor 120 to control the operation of the drive sources 114 to cause the arm 100 to operate. In particular, the software can control the processor 120 to cause the drive sources (for example via distributed controllers) to drive in dependence on inputs from the sensors 116 and from a surgeon command interface 124. The control unit 118 is coupled to the drive sources 114 for driving them in accordance with outputs generated by execution of the software. The control unit 118 is electrically connected to the sensors 116 for receiving sensed input from the sensors, and to the command interface 124 for receiving input from it. The electrical connections described with reference to FIG. 1 and all subsequent figures may, for example, each be electrical or optical cables, or may be provided by a wireless connection.

The command interface 124 comprises one or more input devices whereby a user can request motion of the end effector in a desired way. The input devices, or input controllers, could, for example, be manually operable mechanical input devices such as control handles or joysticks, touch-operable inputs such as touchscreens, or contactless input devices such as optical gesture sensors or voice sensors. The input devices might monitor eye movement to receive an input. The input devices could, for example, be some combination of these types of input devices. Commands input by the input devices can include movement commands, for example to move the instrument in a particular way, such as a lateral movement and/or a rotation. Such commands can include end effector commands, for example to control an end effector coupled to a distal end of the instrument 112 to operate the end effector, such as to open/close gripper jaws or to operate (turn on or off) an electrosurgical end effector.

The software stored in the memory 122 is configured to respond to those inputs and cause the joints of the arm and instrument to move accordingly, in compliance with a predetermined control strategy. The control strategy may include safety features which moderate the motion of the arm and instrument in response to command inputs. Thus, in summary, a surgeon at the surgeon console which suitably comprises the command interface 124 can control the instrument 112 to move in such a way as to perform a desired surgical procedure. Thus, the robot arm 100 functions as a master-slave manipulator where the control unit 118 acts as a master controller. The control unit 118 and/or the command interface 124 may be remote from the arm 100.

Figure 2:
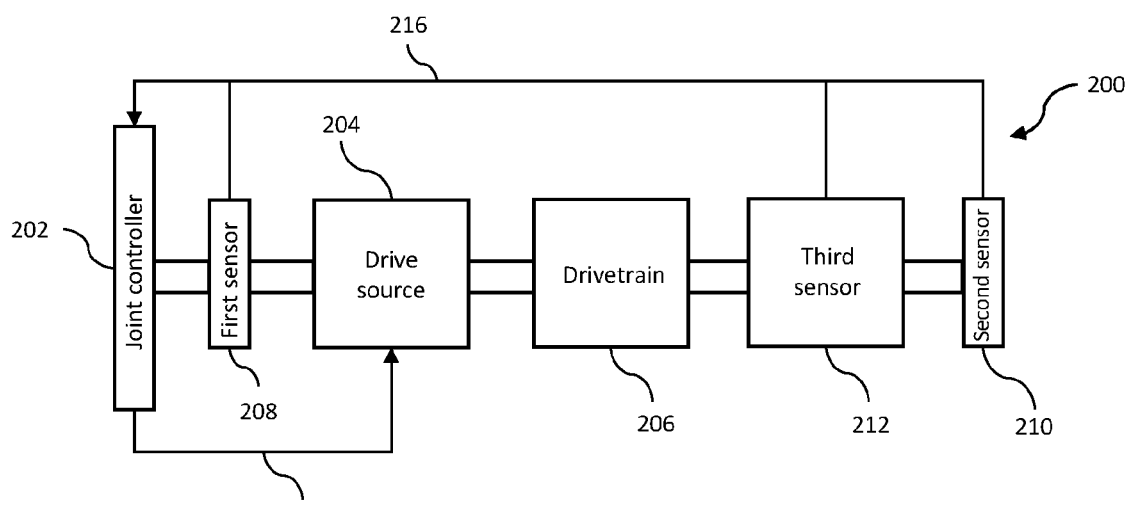
FIG. 2 illustrates a system for controlling the configuration of a joint in a robot arm.

FIG. 2 illustrates a system for controlling the configuration of a joint in a robot arm, such as joints 106a-e illustrated in FIG. 1. The system comprises a joint controller 202, a drive source 204, a drivetrain 206, and sensors 208, 210, 212.

The joint controller 202 is provided to control the configuration of the joint. The joint controller 202 comprises one or more electrical connections for connecting to the drive source 204 and sensors 208, 210, 212 associated with the joint. The joint controller 202 is electrically connected to the sensors 208, 210, 212 by means of one or more feedback loops 216. The feedback loops 216 enable the controller 202 to receive measurements indicating the configuration of the joint from the sensor. The joint controller 202 is connected to the drive source 204 by means of a feedforward loop 214. The joint controller 202 is also connected to the control unit 118 via a feedforward loop, and is configured to receive a reference configuration value $q_{ref}$ from the control unit 118. In one example, the joint controller 202 is a separate entity to the control unit 118. In another example, the joint controller 202 and the control unit 118 are comprised within the same entity. Thus, in this example, the control unit 118 may be directly connected to the sensors 208, 210, 212. The joint controller 202 may be distributed within a robot arm such that it is proximal to a joint that it is configured to control. In one example, the joint controller 202 is configured to control a single joint. In another example the joint controller 202 is configured to control more than one joint.

The joint controller 202 is configured to perform a calculation using the reference position value $q_{ref}$ received from control unit 118 and the feedback value from the sensor 208 to generate a reference torque value $\tau_{ref}$. The reference torque value $\tau_{ref}$ indicates the demanded torque that is required to move the joint to the reference configuration $q_{ref}$. In an example where the drive source 204 is a motor, the reference torque value $\tau_{ref}$ is used to calculate a value of desired current that is to be provided to the drive source 204. This desired current is used to generate an output torque $\tau_o$, which is the actual torque that is experienced by the joint when it is driven by the drive source 204. The drive source 204 may correspond to the drive source 114 illustrated in FIG. 1.

The drive source 204 is connected to the joint controller 202 at a first end, and to the drivetrain 206 at its second end. The drivetrain is configured to transfer power from the drive source 204 to the output of the joint. In one example the drivetrain comprises one or more gears. The one or more gears are used to increase or decrease the torque experienced by the joint from the torque supplied by the drive source 204. In a more specific example, the drivetrain is a harmonic drive.

The system further comprises a plurality of sensors 208, 210, 212. The plurality of sensors 208, 210, 212 may correspond to the one or more sensors 116 illustrated in FIG. 1. The plurality of sensors comprises a first sensor 208, a second sensor 210 and a third sensor 212.

The first sensor 208 is configured to generate a first type of measurement. The first type of measurement indicates the input configuration $q_i$ of the joint. The input configuration $q_i$ is measured at the output of the drive source 204 that is configured to drive the joint. Thus, the first sensor 208 may be located at, or at a location proximal to, a first end of the drivetrain 206, at which the drive source 204 is located. The first sensor is electrically connected to the joint controller 202 by means of a feedback loop 216. The input configuration $q_i$ may be the input position of the joint.

The second sensor 210 is configured to generate a second type of measurement. The second type of measurement indicates the output configuration at the joint $q_o$. The output configuration $q_o$ is measured at the input to the joint. Thus, the second sensor is located at, or at a location proximal to, a second end of the drivetrain 206, at which the joint is located. The second sensor 210 is electrically connected to the joint controller 202 by means of a feedback loop 216. The output configuration $q_o$ may be the output position of the joint.

The third sensor 212 is configured to generate a third type of measurement. The third type of measurement indicates the output torque $\tau_o$ about the joint. The output torque $\tau_o$ is measured at the input to the joint. Thus, the third sensor is also located at, or at a location proximal to, the drivetrain 206. The third sensor 212 is electrically connected to the joint controller 202 by means of a feedback loop 216.

The sensors 208, 210, 212 may be configured to continuously sense data indicating the performance of the joint. This continuous sensing of data may be performed at regular time intervals. That is, the sensing of data from the joint may be performed by the sensors at a predefined sampling rate. This sampling rate may be configurable, such as at the command interface 124 illustrated in FIG. 1. Where the input and output configurations are the input and output positions, respectively, of the joint, the first and second sensors 208, 210 may be position sensors such as linear or rotary encoders.

In theoretical modelling, the drivetrain that actuates a robotic joint can be modelled as "stiff". A stiff drivetrain is one that does not experience any stiction or backlash. Backlash refers to the lost motion that is experienced due to a change in joint direction and is caused by gaps or clearance between interfacing components within the drivetrain. If there is no stiction or backlash in the drivetrain, then the torque generated by the drive source (i.e. the input torque that is provided at the first end of the drivetrain) will always be proportional to the torque that is experienced by the joint (i.e. output torque at the second end of the drivetrain). A method for determining the stiffness of a joint is to compare the difference between input and output configuration to the output torque $\tau_o$ measured for the joint. Ideally, the joint would have a high stiffness and the difference between input and output configuration minimal.

In reality, the components of the drivetrain that actuate a robotic joint are not stiff and have an associated level of elasticity. A joint that is not stiff, when it is driven, experiences an inertia which opposes the output torque $\tau_o$ provided by the drive source. The inertia may be caused by a number of factors that are either internal or external to the joint. An exemplary cause of inertia is the weight of the joint due to gravity. Another exemplary cause is the weight of an object being supported by or interfacing with the joint. Due to presence of inertia, the configuration of the joint at its output $q_o$ may differ from the reference configuration $q_{ref}$. For an elastic joint, there is a degree of elasticity associated with the both the drivetrain 206 and the torque sensor 212. Parameters and disturbances associated with this degree of elasticity have to be accounted for and are highly variable from joint to joint. These variations make it difficult to generate a unified control scheme that can cope for joint differences, and that can determine the cause of disturbances.

Figure 3:
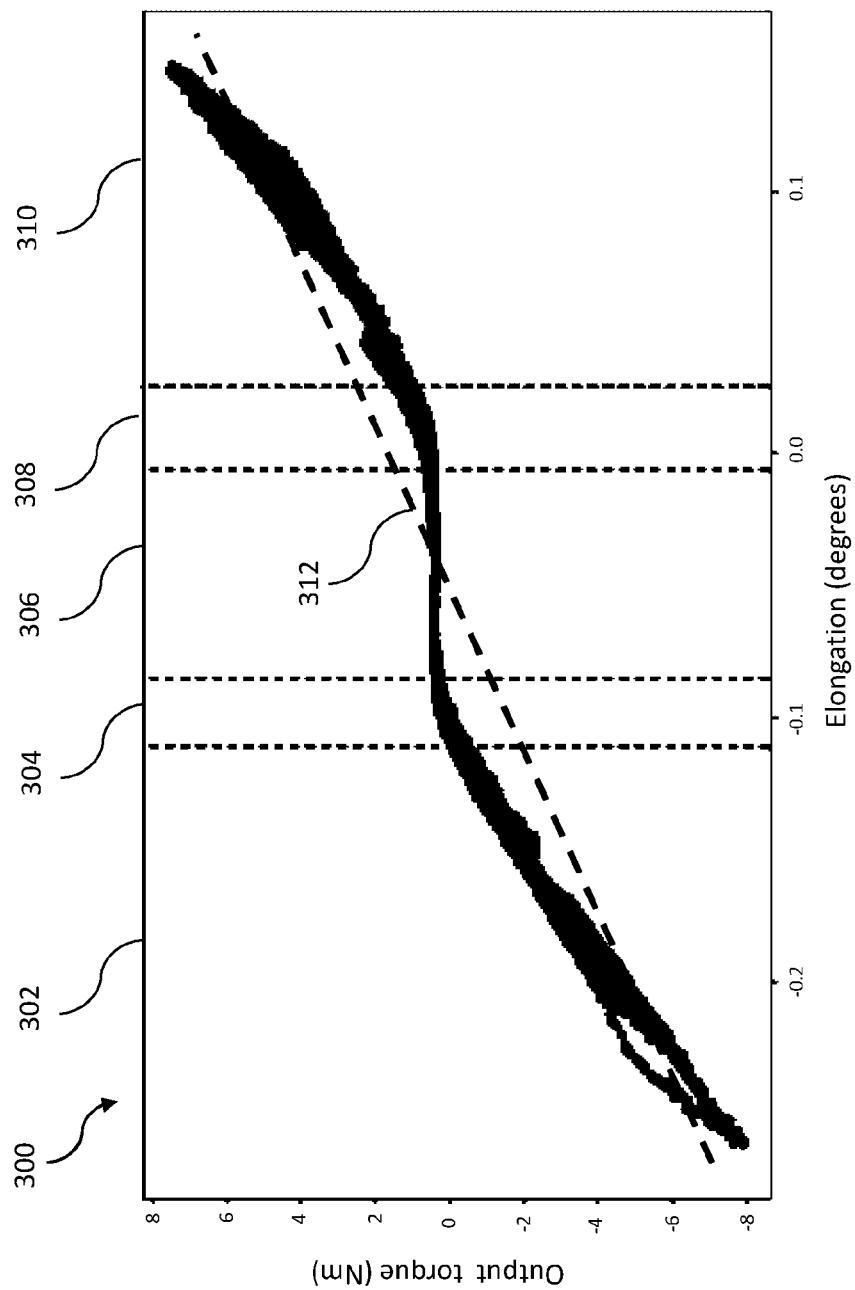
FIG. 3 illustrates the characterisation of the non-linear stiffness of a drivetrain for a robotic joint.

As described above, mechanisms for driving joints within a robotic system comprise an associated element of elasticity, which results in a non-linear stiffness characteristic. This elasticity is especially characteristic of harmonic drives. FIG. 3 is a graph illustrating an exemplary non-linear stiffness characteristic for an elastic rotary joint in a robot arm. The graph plots elongation ε on the x-axis and output torque $\tau_o$ on the y-axis. The output torque $\tau_o$ may be measured by a sensor located at a second end of the drivetrain, at which the joint is located. The sensor for measuring output torque may be a gauge sensor. A gauge sensor is configured to measure changes in voltage due to mechanical strain. Elongation is calculated as the difference between the input configuration $q_i$ and the output configuration $q_o$ of the joint. That is, elongation may defined by the following equation:

$$\varepsilon = q_i - q_o$$

Where $q_i$ is measured at the output of the drive source, and $q_o$ is measured at the input to the joint. In the examples below, elongation is calculated using the above equation. However, it will be appreciated that elongation may also be defined by subtracting input configuration from output configuration (i.e. $\varepsilon = q_o - q_i$)

In FIG. 3, output torque $\tau_o$ is measured in Nm and elongation ε is measured in degrees. In an alternative example, elongation ε may be measured in radians. In both of these examples, the first and second sensors for measuring the input and output configurations are rotary position sensors. In a further example, elongation may be a linear measurement that may be calculated using measurements obtained from linear position sensors. In this example, elongation may be measured in meters. In a further example, elongation may be dimensionless. An example of a dimensionless measurement of elongation is as a percentage.

The graph illustrated in FIG. 3 comprises five distinct regions 302-310. Regions 302 and 310 demonstrate a directly proportional relationship between drivetrain elongation and output torque $\tau_o$. That is, as the elongation of the drivetrain increases, the output torque increases at a constant rate. Region 302 illustrates the joint performance for negative values of elongation, and region 310 illustrates its performance for positive values of elongation. That is, region 302 illustrates joint performance whilst the joint is moving in a first direction, and region 310 illustrates its performance when it is moving in a second direction opposing the first direction. The gradient of the data plot in regions 302 and 310 represents the stiffness K of the drivetrain within the associated range of elongation values. Thus, the relationship between output torque $\tau_o$, elongation ($\varepsilon = q_i - q_o$) and stiffness K can be characterised by the following equation:

$$\tau_o = K(q_i - q_o)$$

Thus, the output torque is characterised by a directly proportional relationship between the elongation ($q_1 - q_o$, and stiffness K of the drivetrain.

Region 306 represents the phenomenon of backlash, where the gradient of data plot representing the stiffness of the drivetrain is near-zero. As described above, backlash refers to the lost motion in a mechanism that is experienced when it changes direction and is caused by gaps or clearance between interfacing components of the drivetrain. For a harmonic drive, backlash is the result of clearance between its circular spline and its flex spline, and/or elastic deformation of the flex spline under torque. This phenomenon typically occurs within a region of elongation values. In the example illustrated in FIG. 3, this region of elongation values is between −0.1 and 0 degrees. It will be appreciated that, for different joints, the backlash region will present itself at a different range of elongation values. In this region of the graph the measured sensor torque is near-zero and does not vary as the elongation increases between −0.1 and 0 degrees. Thus, during the reversal of the joint direction between −0.1 and 0 degrees of elongation no torque is transmitted through the drivetrain from the drive source to the joint. The phenomenon of backlash also occurs in the opposite drive direction, as the elongation decreases from 0 to −0.1 degrees.

Regions 304 and 308 are transition regions, or low displacement stiffness regions. In these regions the drivetrain is transitioning between the backlash region 306 and the regions 302, 310 demonstrating a directly proportional relationship between drivetrain elongation and output torque $\tau_o$. During these regions, there is a non-linear relationship between elongation and sensor torque. These regions occur at joint configurations where not all of the elements of the drivetrain are in contact with one another, and only a small portion of torque from the drive source is being transferred to the joint.

The representative stiffness of the drivetrain throughout the range of elongation values recorded in FIG. 3 is represented by the gradient of a regression line 312 that passes through all regions of the graph. As mentioned above, and clarified in FIG. 3, an elastic joint displays a non-linear relationship between elongation and output torque. That is, the gradient of the stiffness characteristic in the backlash region 306 (which is near-zero) differs substantially from its gradient in regions 302 and 310. Thus, the straight line represented by 312 does provide an accurate representation of the stiffness characteristic of the drivetrain for all values of elongation. In addition to this, the constantly changing relationship between elongation and output torque makes it difficult to model and predict the performance of a joint throughout its full range of motion.

It is desired to provide an accurate indication of when a given joint is performing within, or under, a performance threshold by measuring the performance of its drive train. Thus, it is important to devise a standardised method for characterising joints in this way, and for determining whether those joints (and the robot within which they are comprised) are suitable for use.

Figure 4:
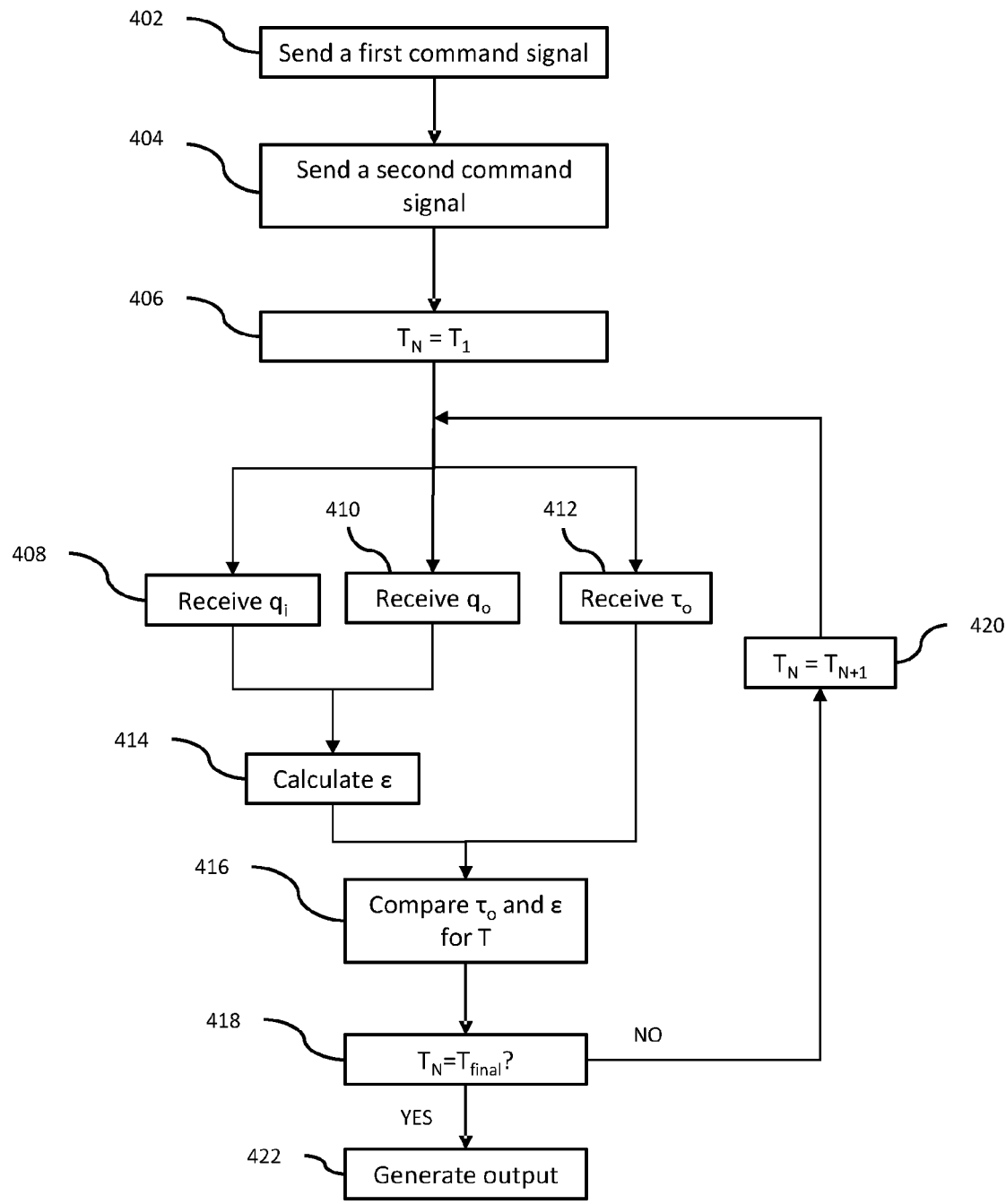
FIG. 4 is a illustrates a method for characterising the performance of a joint in a surgical robotic arm.

FIG. 4 illustrates a method for characterising the performance of a joint in a surgical robotic system. The method illustrated in FIG. 4 may otherwise be referred to as a method for testing the performance of the joint. The method is initiated at step 402, a first command signal is sent to the robot arm. The first command signal may be sent to the joint controller 202. The first command signal comprises an instruction to position the robot arm into an initial configuration. The first command signal may comprise a first reference configuration $q_{ref}$. The first configuration $q_{ref}$ may be calculated by applying one or more inverse kinematic calculations to the commanded end effector pose. In one example, the reference configuration $q_{ref}$ is the desired physical position of the joint. The initial configuration of the arm may be a predetermined configuration. The predetermined configuration may be selected from a set of predetermined configurations. The set of predetermined arm configurations may be selected to ensure that the configuration of the joint is one in which torque and elongation values of interest are reached.

The response of a joint to a predefined force is highly dependent on the configuration of the joint at the time at which the force is applied. That is, the inertial mass of a joint will vary with the configuration of that joint. At some joint configurations a small inertial mass of a joint may enable the joint to be rotated without reaching torques and elongation values of interest. Thus, it is important that the initial configuration of the joint is known before the testing procedure begins. The initial configuration may be selected from a range of configurations at which it is established that torque and elongation values of interest will be reached. Positioning the joint in a predetermined configuration prior to testing also allows for the standardisation and repeatability of that test.

In response to the first command signal 402, the joint is moved into an initial configuration. In one example, the initial configuration is a predetermined configuration. Joint movement may be driven by the drive source 204 and the drivetrain 206. In one example, feedback is sent to indicate that the joint is in the initial configuration. The feedback may comprise measurements obtained from one or more of the sensors 208, 210, 212. Alternatively, it may be determined that the joint is in the initial configuration after a known time period has elapsed. In the steady state, the configuration of the joint does not vary with time.

Once it has been determined that the joint is in the initial configuration, at step 404 a second command signal is sent. The second command signal may be sent to the joint controller 202. The second command signal comprises an instruction to apply a force to the joint. The application of force to the joint displaces the joint from the steady state. In one example, the second command signal 404 indicates a desired configuration for the joint. That is, the second command signal 404 may comprise a second reference configuration $q_{ref}$. The second reference configuration $q_{ref}$ may be calculated by applying one or more inverse kinematic calculations to the commanded end effector pose. In one example, the reference configuration $q_{ref}$ is the desired physical position of the joint. In one example, the displacement of the joint from a steady state results in oscillation of that joint. This oscillation may be the result of natural movement of the joint as it returns to the steady state. Alternatively, the oscillation of the joint may be amplified by the joint controller 202. The oscillation of the joint provides a wide range of varying torque and configuration measurements. In another example, the displacement of the joint does not result in oscillation and the joint may instead return directly to the steady state after displacement. This direct movement may occur in an overdamped joint.

At step 406 a first time interval, $T_N = T_1$, is established. The first time interval may be defined at a time at which a clock is started. The clock may be used to count a predefined time period during which sensor measurements are received from the joint. The time period may start at the time at which the sensor measurements indicate that the joint is displaced from the steady state. The time period may alternatively start when the first command signal is sent, or when the second command signal is sent. The time period may end when the sensor measurements indicate that joint has returned to the steady state. The time period may be predetermined and may be calculated in advance of the test. Alternatively, the time period may be selected by a user in dependence on observations on when the joint returns to the steady state. The time period may be started manually by a user. The number of time intervals that have elapsed since the first time interval $T_N = T_1$ has been established is recorded.

At step 408 a first measurement is received for the first time interval $T_1$. The first measurement indicates the configuration of the drive source at a first end of the drivetrain. That is, the first measurement indicates the input configuration $q_i$ of the joint. The first measurement is measured by the first sensor 208 as illustrated in FIG. 2. In one example, the input configuration is the position of the joint at its input.

At step 410, a second measurement is received for the first-time interval $T_1$. The second measurement indicates the configuration of the joint at a second end of the drivetrain. That is, the second measurement indicates the output configuration $q_o$ of the joint. The second measurement is measured by the second sensor 212 in FIG. 2. In one example, the output configuration is the position of the joint at its output.

At step 412 a third measurement is received for the first time interval $T_1$. The third measurement indicates the torque experienced by the joint at the second end of the drivetrain. That is, the third measurement indicates the output torque $\tau_o$ of the joint. The third measurement is measured by the third sensor 210 illustrated in FIG. 2.

At step 414, a value of elongation for the first time interval $T_1$ is calculated. This value of elongation is calculated using the first and second measurements received for the first time interval $T_1$. As mentioned above, elongation is defined by the following equation:

$$\varepsilon = q_i - q_o$$

This, elongation is calculated by subtracting the second measurement from the first measurement.

At step 416, the values of output torque $\tau_o$ and elongation $\varepsilon$ for the first time interval are compared. This comparison is used to derive a relationship between output torque $\tau_o$ and elongation $\varepsilon$. The relationship between output torque $\tau_0$ and elongation $\varepsilon$ may indicate the stiffness of the joint at the measured elongation value.

At step 418, it is determined whether the first time interval $T_1$ represents the end of the time period. In the example illustrated in FIG. 4, the end of the time period is identified by a predefined final time interval $T_{final}$. In an alternative example, the end of the time period may be identified by a predetermined time (e.g. a predetermined number of seconds after the time period began). In another example, the time period may be ended automatically when it is determined that the joint has returned to the steady state. That is, when sensor data no longer indicates a change in joint configuration over time. In yet a further example, the time period may not be predefined, and may be manually terminated by an operator.

If it is established that the first time interval $T_1$ does not represent the end of the time period, then the method proceeds to step 420. At step 420, a new time interval is selected. That is, $T_N$ is substituted for $T_{N+1}$. Where $T_N$ is the first time interval, $T_1$, then at step 420 $T_1$ is substituted for a second time interval $T_2$. The process of receiving the first, second and third measurements is then repeated for the second time interval $T_2$. Elongation for the second time interval is calculated, and then elongation and output torque are compared. It is then determined whether $T_2$ represents the end of the time period. If 12 does not represent the end of the time period, then a third time interval $T_3$ is selected. Thus, method steps 408-420 are performed iteratively until it is established that a time interval $T_N$ does represent the end of the time period. If this is the case, then the method proceeds to step 422, at which an output is generated.

In the example illustrated in FIG. 4, step 418 occurs after step 416. In an alternative example, step 418 may occur before step 416. That is, output torque and joint configuration measurements may be extracted, but may only be compared after the end of the time period. Step 418 may alternatively occur concurrently with step 416.

Thus, the values of elongation ε and output torque $\tau_o$ are compared at each time interval $T_1, T_2 \ldots T_{final}$. The comparison between these two values at each time interval may be combined to derive a relationship between these two parameters. That is, the sensor data obtained at each time interval may be combined to determine the variation in output torque as elongation varies. This relationship may be derived by selecting a time segment of interest within the predefined time period. This time segment may be selected by identifying a subset of time intervals for which the range of measured elongation and/or output torque values are of interest. The relationship may be further derived by reordering the elongation values so that they are in an ascending order according to their magnitude, as opposed to being in a temporal order. If the elongation values are reordered in this way, then the output torque values associated with each reordered elongation value (i.e. the torque measurement received at the same time interval as the input and output configuration measurements used to calculate elongation) are reordered accordingly.

The comparison between measured values of elongation ε and output torque $\tau_o$ may additionally comprise comparing the relationship between these two parameters to a predetermined characteristic. The predetermined characteristic may be obtained from predetermined theoretical or experimental data. The predetermined characteristic may indicate a desired performance of the joint. Thus, if the derived relationship between elongation ε and output torque $\tau_o$ matches the predetermined characteristic to within a predefined threshold, then it can be determined that the joint is performing within its desired performance threshold. Thus, it can be determined that the joint is suitable for use. If the performance of the joint does not match the predetermined characteristic to within the predefined threshold, it can be determined that the joint is performing under its desired performance threshold.

At step 422, an output is generated indicating the performance of the joint. The output is used to indicate whether the joint is performing within its desired performance threshold. In one example, the output provides a yes/no indication as to whether the joint is performing within the desired performance threshold. In a first example, the output is an audible output. Alternatively, or additionally, the output may be a visual output. The visual output may be a LED indicator, or an alternative indicator light. The visual output may be provided on a display. The output may provide a detailed analysis of the performance of the joint. The output may comprise a command to update the control parameters for the joint.

The second command signal 404 to be provided to the robot arm may otherwise be referred to as an excitation function. Examples of different excitation functions that may be used to displace the joint from the steady state are provided below:

1. The second command signal may comprise an instruction to apply an instantaneous force to the joint, and to displace the joint from the steady state. This type of function is otherwise referred to as a step function. The first, second and third measurements may then be received at a plurality of predefined time intervals whilst the joint returns to the steady state. The time period should end when the joint has returned to the steady state. The instantaneous force may have a large magnitude. That is, the instantaneous force may constitute an aggressive movement with a high acceleration. This allows for a full spectrum of elongation and torque values to be experienced whilst the joint returns to the steady state. This function is preferable for use on joints located closer to the base unit 102 of the robot arm. Joints that are located closer to the base unit are associated with higher inertia values.

2. The second command signal may comprise an instruction to continuously increase the frequency of the force applied to the joint over time. This continuous increase in frequency may occur over a predefined time period. This type of function is otherwise referred to as a chirp function. The first, second and third measurements may then be received at a plurality of predefined time intervals. This excitation function produces large output torque values for the joint, but also produces a large quantity of data at a large range of frequencies. This function is preferable for use on joints located further away from the base unit 102 of the robot arm, or closer to the instrument 112. Joints that are further away from the base unit 102 experience a higher inertia.

3. The second command signal may comprise an instruction to consistently vary the direction of the force to be applied to the joint over a predefined time period. The constant changes in direction will result in an acceleration that will vary the force applied to the joint. The first, second and third measurements may then be received at a plurality of predefined time intervals. As with example 2 above, this function is preferable for use on joints located further away from the base unit 102 of the robot arm, or closer to the instrument 112.

As indicated above, the excitation function to be selected for testing is largely dependent on the joint that is to be observed. Joints that are closer to the base unit 102 of the robot arm experience higher inertias, and so benefit from testing that uses forces with high magnitudes. Joints that are closer to the instrument 112 experience lower inertias and so benefit from testing that uses gradually increasing forces.

In one example, generating an output indicating the performance of the joint comprises calculating a graph of elongation against torque to define a stiffness characteristic for the joint. The graph may be plotted for visualisation on a display. The plotted graph may correspond to that which is illustrated in FIG. 3.

The graph may be outputted to a display located externally to the robot arm. The graph may enable an observer to visualise, compare and analyse results obtained from testing. Thus, the graph may provide a more detailed indication of the performance of the joint. In one example, calculating a graph of elongation against torque further comprises calculating one or more regression lines on the graph of elongation against torque, each regression line being associated with a corresponding gradient. A regression line is a line that best fits its respective data set. As mentioned above, the gradient of a data plot of output torque against elongation represents the stiffness of the drivetrain for the range of elongation values within that data plot. In FIG. 3, the representative stiffness of the drivetrain throughout the range of elongation values recorded in FIG. 3 is represented by the gradient of regression line 312. It is appreciated from FIG. 3 that, for an elastic joint, the relationship between elongation and output torque is not entirely linear. That is, the gradient of the stiffness characteristic in the backlash region 306 (which is zero) differs substantially from its gradient in regions 302 and 310. Thus, the straight line represented by 312 does provide an accurate representation of the stiffness characteristic of the drivetrain for all values of elongation.

A more accurate stiffness characteristic for the drivetrain of a joint can therefore be determined by deriving a plurality of regression lines for a graph of elongation against torque. The plurality of gradients can be used to identify a plurality of distinct regions on the graph. Each region is associated with a different value of stiffness. Regions can be described quantitatively by means of curve/line fitting and compared with some optimal/expected threshold and ideal curves. Regions may alternatively be identified by applying signal conditioning to the received sensor measurements. Signal conditioning enables regions to be detected with greater accuracy.

In one example the graph of elongation against torque can be separated into three regions. The three regions can be defined as follows:

1. A first linear relationship between elongation and torque in a first direction;
2. A second linear relationship between elongation and torque in a second direction; and
3. The backlash region.

The first, second and third regions of the graph may be identified using predefined "breakpoints". A "breakpoint" may be characterised by a predetermined elongation value, or by a predetermined torque value. For example, for a first torque value of zero (or near-zero) the start of the backlash region of the graph may be identified. Alternatively, the first, second and third regions of the graph may be identified by applying a piece-wise fit to the graphical data. That is, where a substantial variation in the relationship between output torque and elongation is identified, a new region may be defined. In this example, the first and second regions as summarised above can be identified by an elongation-torque relationship that can be approximated by a regression line with a gradient that is above a predetermined threshold. By comparison, the backlash region may be identified by a regression line with a gradient that is below a predetermined threshold. The gradient of the regression line approximating the backlash region may be near-zero. A near-zero gradient is one where minimal variation in torque is experienced with larger variation in elongation, relative to the variation in torque with elongation outside of the backlash region. The graphical data may be characterised by a piecewise function.

To demonstrate the difference between the gradient of a regression line characterising the backlash region and the gradients of regression lines outside of this region, the following example is considered. For a specific joint in a robot arm, the elongation of its drivetrain may vary between 2 and −2 degrees. Within this range, the values of elongation that are of interest for the purpose of characterising the performance of that joint may be between −0.5 and 0.5 degrees. The backlash region may occur between −0.1 and 0.1 degrees. So, relative to the total range of elongation values of interest, the backlash region occurs within a large subrange of those values. That is, the range of elongation values in the backlash region relative to the overall range of elongation values of interest is large. The range of torque values of interest for the specific joint in this example may vary from −15 to 15 Nm. The range of torques associated with the backlash region may vary between −0.1 and 0.1 Nm. That is, relative to the total range of torques of interest that are observed, the variation in torque over the backlash region is small. So, on a graph of elongation against torque, in the backlash region, the range of elongation values is relatively large, and the range of torque values is relatively small. The gradient of a regression line in the backlash region, which characterises the variation of torque with elongation, may be close to zero relative to the gradients of regression lines outside of this region (e.g. in the first and second regions described above). For example, for a specific joint in a robot arm, the gradient of a regression line characterising the backlash region may have a maximum value of 15N m/degree. In other words, the backlash region may be identified by a regression line with a gradient that is below a predetermined threshold of 15 Nm/degree. A normal stiffness region, such as the first and second regions described above, may be identified by a regression line with a gradient that is above this predetermined threshold of 15 Nm/degree. More commonly, a normal stiffness region may have a gradient of greater than 50 Nm/degree. The gradient of the regression line in the backlash region can therefore be described as near-zero, relative to the gradient of its surrounding regions. The above values are provided as examples only, as it is appreciated that for different joints, the backlash region will present itself at a different range of elongation values.

In an alternative example, the graph of elongation against torque can be separated into five regions. The five regions can be defined as followed:

1. A first linear relationship between elongation and torque in a first direction;
2. A first low displacement stiffness region in a first direction;
3. A second linear relationship between elongation and torque in a second direction;
4. A second low displacement stiffness region in a second direction; and
5. The backlash region.

These five regions are described in greater detail with reference to FIG. 3. The five distinct regions may be identified using "breakpoints" or piecewise fits, as described above. It would be understood that more or fewer regions than those specified herein can be derived from a graph indicating the stiffness characteristics of a joint. For example, some joints may have more than one associated backlash region over a range of elongation values.

The graph may be further analysed to establish the accuracy of the one or more regression lines. In one example, the accuracy of the one or more regression lines can be determined using an R-squared statistic. An R-squared statistic is used to evaluate the distribution of data points around the regression line and determine how accurate the line is at representing the graphical data. Thus, the R-squared analysis may be used to determine the accuracy of the one or more regression lines in representing the graphical data. In alterative examples, the accuracy of the one or more regression lines may be determined using a signal-to-noise, polynomial, least squares or any other known analysis method.

In one example, the method described in FIG. 4 may be commanded by a testing unit located externally to the robot arm. The testing unit may comprise software with instructions to execute the test as illustrated in FIG. 4. That is, the testing unit may be connected to the robot arm so that it can send the first and second command signals to the robot arm and can receive sensor measurements from the robot arm. Alternatively, the method described in FIG. 4 could be commanded from the control unit 118. In this example, a user may instruct the initiation of the test at the command interface 124. The control unit 118 may then send the first and second command signals to the robot arm and receive sensor measurements from the robot arm as instructed. The control unit may comprise a plurality of special control parameters for performing the method described in FIG. 4. These control parameters may differ from the parameters used during normal operation of the robot arm. With the concept of the invention it is possible to obtain the characteristic graph for the joint during a procedure or during Power on Self-Test (POST) before the system is operational, compare the plot against that of an ideal joint and determine whether the joint is suitable for use.

The method described in FIG. 4 may be performed during an initialisation protocol for a robot arm. Alternatively, the method may be performed during routine testing of the arm. The method may be performed during manufacture of the arm.

The above methods can be used to fully characterise the performance of a joint using the sensors and drive mechanisms provided within the robot arm. That is, no further sensors or rigs are required to characterise the drivetrain of the joint. This differs from robotic systems that do not comprise two configuration sensors. For such robotic systems, it would be necessary to lock one of the ends of the drivetrain while forcing the other end of the drivetrain to rotate in order to measure torque at the unlocked end of the drivetrain, and therefore to derive a stiffness characteristic for the joint. Thus, the methods described herein provide a simple, quick and reliable method for characterising the performance of a joint in a robotic arm. In dependence on the derivation of joint performance, it may be possible to vary control parameters during operation of the joint to account for this performance. Alternatively, this derivation may be used to determine that a joint is not suitable for use, or that it requires maintenance.

FIGS. 3 and 4, as described above, refer to the forces applied to and measured from a joint as being torques. Thus, FIGS. 3 and 4 refer to methods for controlling and measuring the configuration of a rotary joint. In an alternative example, the joint to be controlled may be configured to provide linear motion. In this example, corresponding forces can be measured and calculated using strain gauges or other force sensors.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A method for characterising the performance of a joint in a surgical robotic arm, the joint being driven by a drivetrain which transfers power from a drive source to the joint, the method comprising:
   sending a first command signal to position the robot arm into an initial configuration;
   sending a second command signal to apply a force to the joint to displace the joint from a steady state;
   for a plurality of predefined time intervals:
      receiving a first measurement indicating the configuration of the drive source at a first end of the drivetrain;
      receiving a second measurement indicating the configuration of the joint at a second end of the drivetrain;
      calculating a value of elongation using the first and second measurements; and
      receiving a third measurement indicating the torque experienced by the joint at the second end of the drivetrain;
   comparing the values of elongation with corresponding values of the measured torque at each of the predefined time intervals; and
   generating an output from the comparison indicating the performance of the joint.

2. The method as described in claim 1, wherein generating the output comprises calculating a graph of elongation against torque to define a stiffness characteristic for the joint.

3. The method as claimed in claim 1, further comprising comparing the values of elongation and corresponding values of torque to a predetermined characteristic for the joint.

4. The method as claimed in claim 1, wherein the method comprises:
   sending a command signal to apply an instantaneous force to the displace the joint from the steady state; and
   receiving the first, second and third measurements at a plurality of predefined time intervals whilst the joint returns to the steady state.

5. The method as claimed in claim 1, wherein the method further comprises:
   sending a command signal to consistently increase the frequency of the force applied to the joint; and
   receiving the first, second and third measurements at a plurality of predefined time intervals.

6. The method as claimed in claim 1, wherein the method further comprises:
   sending a command signal to consistently vary the direction of the force to be applied to the joint; and
   receiving the first, second and third measurements at a plurality of predefined time intervals.

7. The method as claimed in claim 1, wherein the second command signal indicates a desired configuration for the joint.

8. The method as claimed in claim 1, wherein elongation is characterised as the difference between the measured configuration of the drive source $q_i$ and the measured configuration of the joint $q_o$.

9. The method as claimed in claim 2, further comprising calculating one or more regression lines on the graph of elongation against torque, each regression line having a corresponding gradient.

10. The method as claimed in claim 9, wherein the method further comprises analysing the gradients of the one or more regression lines to identify a plurality of distinct regions.

11. The method as claimed in claim 10, wherein the method further comprises identifying a backlash region from the graph, the backlash region being characterised a regression line with a near-zero gradient.

12. The method as claimed in claim 8, wherein the method further comprises identifying one or more linear stiffness regions from the graph, each linear stiffness region being identified by a regression line with a gradient that is above a predetermined threshold.

13. The method as claimed in claim 9, the method further comprising analysing the graph to establish the accuracy of the one or more regression lines.

14. The method as claimed in claim 13, wherein analysing the graph comprises performing an R-squared analysis.

15. The method as claimed in claim 10, wherein the plurality of distinct regions are identified by applying signal conditioning to the received sensor measurements.

16. The method as claimed in claim 1, wherein the drive source is a motor.

17. The method as claimed in claim 1, wherein the initial configuration of the arm is selected from a set of predetermined arm configurations.

18. The method as claimed in claim 1, wherein the drivetrain comprises one or more gears.

19. The method as claimed in claim 1, wherein the drivetrain is a harmonic drive.

* * * * *